United States Patent
Fujinuma

(10) Patent No.: US 12,215,435 B2
(45) Date of Patent: Feb. 4, 2025

(54) ELECTROCHEMICAL CELL, METHOD FOR PRODUCING CARBONYL COMPOUND, AND SYNTHESIS SYSTEM

(71) Applicant: SEKISUI CHEMICAL CO., LTD., Osaka (JP)

(72) Inventor: Naohiro Fujinuma, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 17/940,542

(22) Filed: Sep. 8, 2022

(65) Prior Publication Data

US 2023/0095968 A1 Mar. 30, 2023

Related U.S. Application Data

(60) Provisional application No. 63/242,297, filed on Sep. 9, 2021.

(51) Int. Cl.
*C25B 3/07* (2021.01)
*B01J 19/08* (2006.01)
*C07C 68/01* (2020.01)
*C25B 9/19* (2021.01)

(52) U.S. Cl.
CPC ............... *C25B 3/07* (2021.01); *B01J 19/087* (2013.01); *C07C 68/01* (2020.01); *C25B 9/19* (2021.01); *B01J 2219/0803* (2013.01); *B01J 2219/0884* (2013.01); *B01J 2219/0892* (2013.01)

(58) Field of Classification Search
None
See application file for complete search history.

(56) References Cited

U.S. PATENT DOCUMENTS

| | | | |
|---|---|---|---|
| 5,296,106 A * | 3/1994 | Rolison | B01J 35/33 205/334 |
| 2020/0095692 A1 * | 3/2020 | Fujinuma | C25B 1/00 |
| 2021/0246562 A1 * | 8/2021 | Klein, Jr. | C25B 3/07 |

OTHER PUBLICATIONS

Anastasiadou et al. (Chem. Commun.,2020, 56, 13082) (Year: 2020).*
Akiyasu Funakawa et al., "High Efficient Electrochemical Carbonylation of Methanol to Dimethyl Carbonate by $Br_2/Br^-$ Mediator System over Pd/C Anode", Journal of The Electrochemical Society, 153 (4), pp. D68-D73, 2006.
Akiyasu Funakawa et al., "Active Control of Methanol Carbonylation Selectivity over Au/Carbon Anode by Electrochemical Potential", J. Phys. Chem. B, vol. 109, No. 18, pp. 9140-9147, 2005.
Marta C. Figueiredo et al., "Spectro-Electrochemical Examination of the Formation of Dimethyl Carbonate from CO and Methanol at Different Electrode Materials", J. Am. Chem. Soc., 139, pp. 14693-14698, 2017.

(Continued)

*Primary Examiner* — Wojciech Haske
(74) *Attorney, Agent, or Firm* — Wenderoth, Lind & Ponack, L.L.P.

(57) ABSTRACT

The electrochemical cell is an electrochemical cell which electrochemically synthesizes at least one carbonyl compound selected from the group consisting of organic carbonates and organic oxalates from carbon monoxide, and has an electrolyte solution containing a redox species and a catalyst, and an electrode.

15 Claims, 2 Drawing Sheets

(56) References Cited

OTHER PUBLICATIONS

Tao-Tao Zhuang et al., "Dopant-tuned stabilization of intermediates promotes electrosynthesis of valuable C3 products", Nature Communications, 10:4807, pp. 1-7, 2019.
Yamanaka, Ichiro et al., "Electrocatalytic synthesis of DMC over the Pd/VGCF membrane anode by gas-liquid-solid phase-boundary electrolysis", Journal of Catalysis, 2004, vol. 221, 110-118.

* cited by examiner

[Fig. 1]
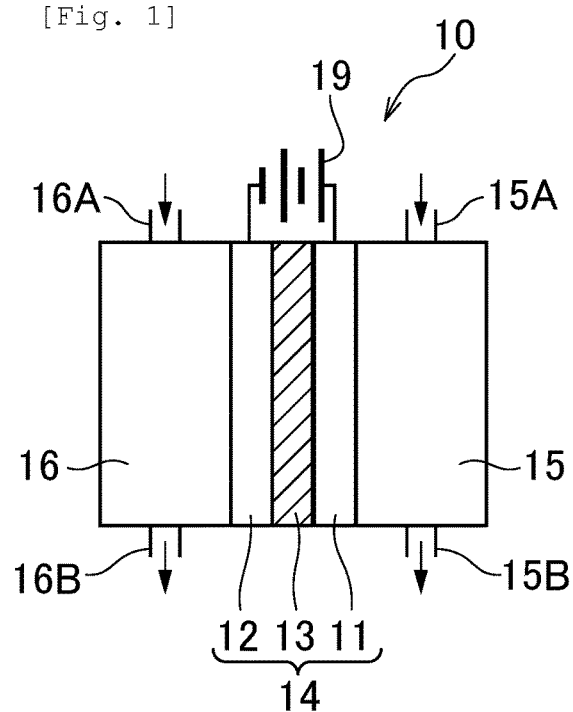
[Fig. 2]
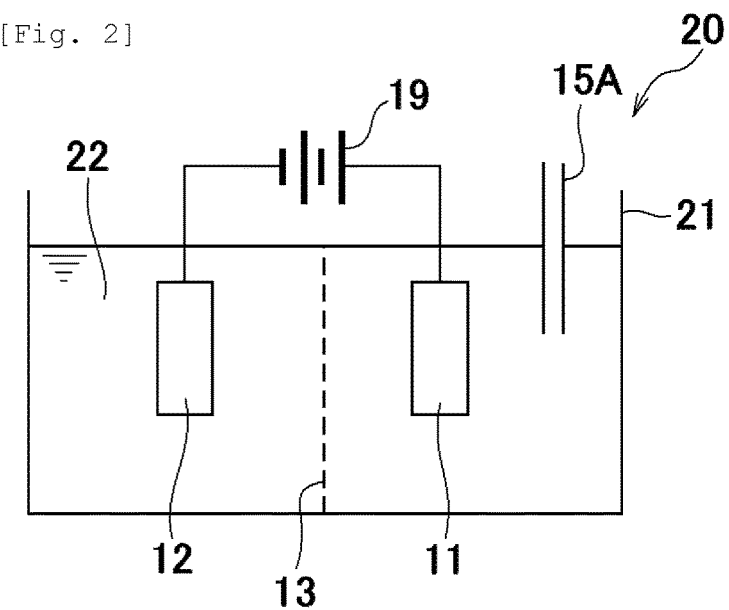

[Fig. 3]
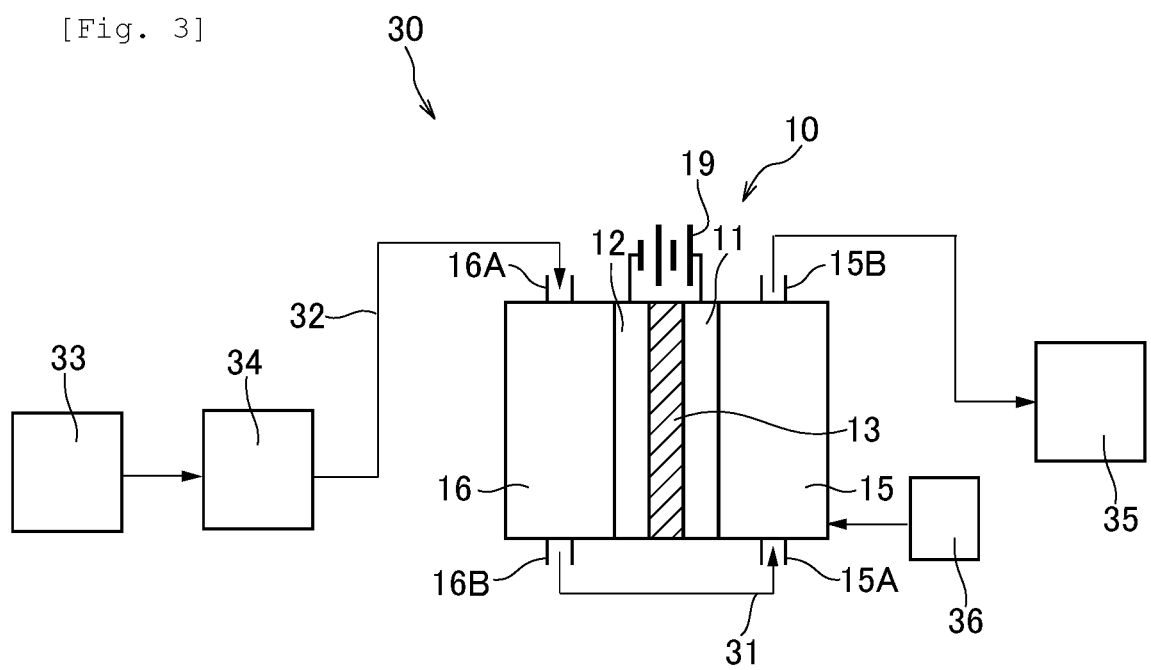

ELECTROCHEMICAL CELL, METHOD FOR PRODUCING CARBONYL COMPOUND, AND SYNTHESIS SYSTEM

FIELD OF THE INVENTION

The present invention relates to an electrochemical cell for electrochemically synthesizing at least either one of an organic carbonate and an organic oxalate from carbon monoxide, and a method of producing a carbonyl compound and a synthesis system for producing at least either one of an organic carbonate and an organic oxalate from carbon monoxide.

BACKGROUND OF THE INVENTION

Organic carbonates are being utilized in various fields such as coating materials, adhesive agents, electrolyte solutions and resin raw materials. Conventional synthesis methods of organic carbonates utilize a highly poisonous raw material such as phosgene or an explosive oxygen mixed gas, and often form highly poisonous wastes. Hence, in recent years, for the synthesis of organic carbonates, a new synthesis method low in environmental load has been desired.

On the other hand, electrochemical synthesis methods do not need a highly poisonous reactant and a highly explosive oxygen mixed gas, and since electricity can be made use of directly from renewable energy, have recently been highlighted. Further, in recent years, for the purpose of suppression of global warming and substitutes for fossil fuels and the like, it has been studied to form organic substances by electrochemical reactions by using, as a raw material, carbon dioxide or carbon monoxide obtained by reducing carbon dioxide. Also for organic carbonates, there have been attempted electrochemical syntheses using carbon monoxide or the like as a raw material and using various catalysts (for example, see Non Patent Literature 1: Journal of Catalysis, 2004 110-118, Non Patent Literature 2: Journal of Electrochemical Society, 153(4), D68 (2006), Non Patent Literature 3: J. Phys. Chem. B 2005, 109, 9140-9147, Non Patent Literature 4: J. Am. Chem. Soc. 2017, 139, 14693-14698, Non Patent Literature 5: Nat Commun 10, 4807 (2019).

The conventional electrochemical synthesis methods of organic carbonates, however, are low in selectivity, and the improvement in the selectivity is needed for practical use. In the electrochemical synthesis of organic carbonates, a catalyst is usually made to be contained in an electrode in many cases, and in these cases, the production of the electrode becomes intricate and synthesis of organic carbonates by a simpler method is demanded.

Further since carbonyl compounds are useful as intermediates of various kinds of compounds in addition to the organic carbonates, it is desired that also for organic oxalates, a new synthesis method low in environmental load is established.

Then, the present invention has an object to provide an electrochemical cell which can electrochemically synthesize at least either one carbonyl compound of an organic carbonate and an organic oxalate in a high selectivity from carbon monoxide, by a simple constitution low in environmental load, a method for producing the carbonyl compound, and a synthesis system.

SUMMARY OF THE INVENTION

The present invention provides the following [1] to [14].
[1] An electrochemical cell which electrochemically synthesizes at least one carbonyl compound selected from the group consisting of organic carbonates and organic oxalates from carbon monoxide, the electrochemical cell comprising: an electrolyte solution comprising a redox species and a catalyst; and an electrode.
[2] The electrochemical cell according to the above [1], wherein the catalyst comprises at least one metal element selected from the group consisting of group 8 to group 11 elements.
[3] The electrochemical cell according to the above [1], wherein the catalyst comprises at least two metal elements selected from the group consisting of group 8 to group 11 elements.
[4] The electrochemical cell according to any one of the above [1] to [3], wherein the catalyst is at least one selected from the group consisting of metal salts and catalysts comprising an active particle having a metal element.
[5] The electrochemical cell according to any one of the above [1] to [4], wherein the redox species is at least one selected from the group consisting of halogenated metal salts, organic redoxes and complex redoxes.
[6] The electrochemical cell according to any one of the above [1] to [5], wherein the electrode comprises no catalyst.
[7] The electrochemical cell according to any one of the above [1] to [6], wherein the electrolyte solution comprises an alcohol-based compound.
[8] The electrochemical cell according to any one of the above [1] to [7], further comprising: an anode compartment comprising the electrode disposed therein and containing the electrolyte solution therein; and an inlet port through which carbon monoxide is supplied to the anode compartment.
[9] The electrochemical cell according to any one of the above [1] to [8], comprising dispersing member bubbling, fluidizing or stirring the electrolyte solution to disperse at least either one of the catalyst and the redox species in the electrolyte solution.
[10] A method of producing a carbonyl compound, comprising electrochemically synthesizing at least one carbonyl compound selected from the group consisting of organic carbonates and organic oxalates from carbon monoxide in an electrochemical cell according to any one of the above [1] to [9].
[11] The method of producing a carbonyl compound according to the above [10], comprising converting carbon dioxide into carbon monoxide, the carbonyl compound being electrochemically synthesized from the carbon monoxide.
[12] The method of producing a carbonyl compound according to the above [11], wherein the carbon dioxide is obtained from any one of exhaust gases of electric power plants, ironworks, cement factories and waste incineration plants.
[13] A synthesis system comprising an electrochemical cell according to any one of the above [1] to [9],
wherein the synthesis system comprises a conversion portion which converts carbon dioxide to carbon monoxide and a supply path which supplies the carbon monoxide obtained by the conversion portion to the anode compartment.
[14] The synthesis system according to the above [13], wherein the carbon dioxide is obtained from any one of exhaust gases of electric power plants, ironworks, cement factories and waste incineration plants.

According to the present invention, at least either one carbonyl compound of an organic carbonate and an organic oxalate can be electrochemically synthesized in a high selectivity from carbon monoxide, by a simple constitution low in environmental load.

BRIEF DESCRIPTION OF THE DRAWINGS

FIG. 1 is a schematic diagram illustrating a specific example of the electrochemical cell of the present invention;

FIG. 2 is a schematic diagram illustrating another specific example of the electrochemical cell of the present invention; and FIG. 3 is a schematic diagram illustrating an embodiment of the synthesis system of the present invention.

DETAILED DESCRIPTION OF THE INVENTION

<Electrochemical Cell>

The electrochemical cell of the present invention is an electrochemical cell which electrochemically synthesizes at least one compound (hereinafter, referred to as "carbonyl compound" in some cases) selected from the group consisting of organic carbonates and organic oxalates from carbon monoxide, and has an electrolyte solution (hereinafter, referred to also as "catalyst-containing electrolyte solution") containing a redox species and a catalyst, and an electrode (hereinafter, referred to also as "first electrode").

The electrochemical cell of the present invention, due to containing a redox species and a catalyst in the electrolyte solution, can synthesize a carbonyl compound(s) composed of an organic carbonate, an organic oxalate or both thereof in a high selectivity from carbon monoxide, by a simple constitution low in environmental load.

It is suitable that the catalyst-containing electrolyte solution is made to be contained in the electrochemical cell so as to contact with the first electrode, and it is preferable that the catalyst-containing electrolyte solution is contained in an anode compartment the electrochemical cell has. It is more preferable that the electrochemical cell further has an inlet port through which carbon monoxide is supplied to the cell (typically, anode compartment).

In the electrochemical cell, by applying a voltage between the first electrode constituting an anode and a second electrode constituting a cathode, there occurs an electrochemical reaction in which carbon monoxide is converted into a carbonyl compound in the catalyst-containing electrolyte solution. The first electrode is referred to also as an electrode for synthesizing the carbonyl compound, hereinafter in some cases.

[Catalyst]

The catalyst contained in the catalyst-containing electrolyte solution is not especially limited as long as being capable of catalyzing the electrochemical reaction of synthesizing an organic carbonate, an organic oxalate or both thereof from carbon monoxide, but it is suitable to contain a metal element, and among metal elements, it is preferable to contain a metal element selected from the group consisting of group 8 to group 11 elements. Use of the group 8 to group 11 elements for the catalyst makes easy the electrochemical synthesis of the carbonyl compound from carbon monoxide in a high selectivity.

The group 8 to group 11 elements to be used for the catalyst specifically include Fe, Co, Ni, Cu, Ru, Rh, Pd, Ag, Os, Ir, Pt and Au. Among these, preferable are Co, Ni, Cu, Rh, Pd, Ag, Ir, Au and Pt; and among these, more preferable are Pd, Au, Ag and Ir. By using each element described above, it is easy to electrochemically synthesize an organic carbonate, an organic oxalate or both thereof from carbon monoxide in a high selectivity. From these viewpoints, as the metal element to be contained in the catalyst, Au or Pd is still more preferable and Pd is especially preferable.

The metal element to be used for the catalyst may be used singly in one kind or may be used concurrently in two or more kinds. In the case of concurrent use of two or more kinds, there may be used concurrently two or more kinds of metal elements selected from the group consisting of group 8 to group 11 elements; or there may be used concurrently a metal element in the group 8 to group 11 elements and a metal element other than the group 8 to group 11 elements. The metal element other than the group 8 to group 11 elements includes preferably metal elements of period 4 elements, but may be a metal element other than the metal elements of period 4 elements.

Specifically, preferable is a combination of Au with at least one kind selected from the group consisting of Ti, Mn, Fe, Co, Ni, Cu and Zn. Also preferable is a combination of Pd with at least one kind selected from the group consisting of Ti, Co, Ni, Cr, Mn, Fe, Cu, Zn, Ru, Rh, Ag, Ir, Pt, Au and Sn. Further, also preferable is a combination of Ir with at least one kind selected from the group consisting of Au, Rh and Ru. According to these combinations, while the amount of noble metals to be used can be suppressed, the selectivity when the carbonyl compound is synthesized can be retained high.

From the viewpoint of improvement in the selectivity, in the case of concurrent use of two or more kinds, it is preferable that the metal element to be used for the catalyst contains at least two kinds of metal elements selected from the group consisting of group 8 to group 11 elements. Among these, it is more preferable to concurrently use one of Pd or Ir, and at least one kind other than the one of Pd or Ir, selected from the group consisting of the group 8 to group 11 elements. Specifically, preferable is a combination of Pd with at least one kind selected from the group consisting of Ag, Au, Pt, Ir and Cu, or a combination of Ir with one kind selected from the group consisting of Au, Rh and Ru.

In the case of using a combination of two or more kinds of metals, the content of each metal may suitably be set; however, in the case of using Pd, the content of Pd is, for example, 10 to 99% by mol, and is, from the viewpoint of the selectivity, preferably 25 to 95% by mol. In this case, the content of a metal other than Pd (for example, at least one kind selected from the group consisting of Ag, Au, Pt, Ir and Cu) is, for example, 1 to 90% by mol and preferably 5 to 75% by mol.

In the case of using Ir except for a combination with Pd, the content of Ir is, for example, 5 to 99% by mol, and is, from the viewpoint of the selectivity, preferably 10 to 95% by mol and more preferably 25 to 90% by mol. In this case, the content of a metal other than Ir (for example, at least one kind selected from the group consisting of Au, Rh and Ru) is, for example, 1 to 95% by mol, preferably 5 to 90% by mol and more preferably 10 to 75% by mol.

Then, the content of a metal mentioned herein is a proportion of the metal with respect to the total amount of metals contained in the catalyst.

(Metal Salt)

In the catalyst, the metal element may be contained in a form of a metal ion in the electrolyte solution, or may also be contained in a form other than the metal ion in the electrolyte solution.

In one embodiment, it is preferable that the catalyst is a metal salt and the catalyst is blended as a metal salt in the electrolyte solution. The metal salt includes metal nitrate salts, metal sulfate salts, metal chlorides, metal bromides, metal iodides and metal acetate salts, and among these, metal chlorides and metal nitrate salts are preferable and metal chlorides are more preferable. The metal nitrate salts specifically include cobalt nitrate ($Co(NO_3)_2$), nickel nitrate ($Ni(NO_3)_2$), copper nitrate ($Cu(NO_3)_2$), rhodium nitrate ($Rh(NO_3)_3$), palladium nitrate ($Pd(NO_3)_2$), silver nitrate ($AgNO_3$), iridium nitrate ($Ir(NO_3)_4$), platinum nitrate ($Pt(NO_3)_4$), gold nitrate ($AuNO_3$), ruthenium nitrate ($Ru(NO_3)_3$), iron nitrate ($Fe(NO_3)_3$), manganese nitrate ($Mn(NO_3)_2$), zinc nitrate ($Zn(NO_3)_2$), chromium nitrate ($Cr(NOs)_3$) and tin nitrate ($Sn(NOs)_4$).

Specific examples of the metal chlorides include $PdCl_2$, $RuCl_3$, $IrCl_3$, $PtCl_4$ and $AuCl_3$. The metal chloride may also be $HAuCl_4$ or the like. Among these, $PdCl_2$, $HAuCl_4$ and $Ir(III)Cl_3$ are preferable.

The metal salt may be used singly in one kind, or may also be used concurrently in two or more kinds.

In the present invention, it is preferable that by blending a metal salt as the catalyst in the electrolyte solution, the electrolyte solution contains one or two or more kinds selected from the group consisting of a nitrate ion, a sulfate ion, a chloride ion, a bromide ion, an iodide ion and a hydroxide ion; among these, it is more preferable to contain a chloride ion or a nitrate ion, and it is still more preferable to contain a chloride ion. Further, the metal salt may also be a hydrate.

(Active Particle-Containing Catalyst)

In one embodiment, it is preferable that the catalyst is a catalyst containing an active particle having the above metal element (hereinafter, referred to also as "active particle-containing catalyst"). In this case, it is more preferable that the active particle-containing catalyst further contains a support and the active particle is supported on the support.

The support to be used for the active particle-containing catalyst is not especially limited, but from the viewpoint that the carbonyl compound can be synthesized in a high selectivity from carbon monoxide, a porous carbon is preferable. Therefore, in one embodiment, it is preferable that the catalyst to be contained in the electrolyte solution is a catalyst comprising the active particle having the metal element and the porous carbon which supports the active particle.

In the present invention, the catalyst may be used singly in one kind, or may be used concurrently in two or more kinds, and for example, the above-mentioned metal salt and active particle-containing catalyst may be used concurrently.

Hereinafter, by taking, as examples, the active particle-containing catalyst having the active particle and the porous carbon as the support, the active particle-containing catalyst will be described in detail. The active particle-containing catalyst, as described later, can be produced by mixing and heat-treating a metal precursor and a porous carbon (support). The metal precursor becomes an active particle by the heat treatment, and the active particle is supported on the porous carbon (support).

The active particle in the active particle-containing catalyst has a catalytic ability of catalyzing a reaction of electrochemically synthesizing an organic carbonate, an organic oxalate or both thereof from carbon monoxide. The active particle containing the metal element may be constituted, for example, of a metal oxide, of a metal itself, or of both of a metal oxide and a metal. The metal element to be used for the active particle is as described above.

In the catalyst, the active particle is microparticulate, and it is suitable that the microparticulate active particle is supported on the porous carbon. The active particle is not especially limited, but is a nano-order particle, and it is suitable to have an average particle diameter of preferably 100 nm or smaller, more preferably 1 nm or larger and 40 nm or smaller. By making the active particle to have the above particle diameter and to be nano-structured, the active area is increased, making it easy for various performance features to be improved. Here, the particle diameter means an equivalent circular area diameter obtained by determining the area of each particle and calculating the diameter of a circle having an area equal to the area of the particle.

In the active particle-containing catalyst, the porous carbon is a support to support the above active particle. Due to that the support is the porous carbon, a reactant described later is suitably diffused in the catalyst, making it easy for the selectivity, the reaction efficiency and the like in synthesis of the carbonyl compound to be improved. The porous carbon is not especially limited, but it is preferable that the porous carbon is composed of a powdery or particular carbon compound and in its turn, it is suitable that the catalyst is also powdery or particular. When the catalyst is powdery or particulate, it becomes easy for the catalyst to be dispersed in the electrolyte solution and it becomes easy for the contact area with carbon monoxide to become large, making it easy for the selectivity, the reaction efficiency and the like in synthesis of the carbonyl compound to be improved.

The BET specific surface area of the porous carbon is, for example, 10 $m^2/g$ or larger and 3,000 $m^2/g$ or smaller, and preferably 100 $m^2/g$ or larger and 1,500 $m^2/g$ or smaller. Due to that the surface area of the porous carbon is in the above range, the active particle in a suitable amount is supported on the porous carbon, thereby making the catalyst to have a suitable catalytic activity and making it easy for the selectivity, the reaction efficiency and the like in synthesis of the carbonyl compound to be enhanced. The BET specific surface area of the catalyst can be measured by gas adsorption analysis.

The average primary particle diameter of the porous carbon is, for example, 1 nm or larger and 1,000 nm or smaller and preferably 10 nm or larger and 300 nm or smaller. Due to that the average primary particle diameter of the porous carbon is in the above range, the nano-size active particle is suitably supported on the porous carbon, making it easy for the selectivity, the reaction efficiency and the like in synthesis of the carbonyl compound to be enhanced. Further, it becomes easy for the catalyst to be dispersed in the electrolyte solution. The average primary particle diameter of the porous carbon can be measured, for example, by observation with an electron microscope or the like; specifically, the measurement method includes means for determining the equivalent circular area diameter by determining the area of each particle and calculating the diameter of a circle having an area equal to the area of the particle.

The average pore diameter of the porous carbon is, for example, 0.5 nm or larger and 100 nm or smaller and preferably 1 nm or larger and 50 nm or smaller. Due to that the average pore diameter is in the above range, it becomes easy for the reactant to be diffused in the catalyst and it becomes easy for the selectivity of the organic carbonate and the like, the reaction efficiency and the like to be improved. Here, the average pore diameter of the porous carbon can be measured by gas adsorption analysis.

The porous carbon is not especially limited as long as being capable of supporting the active particle, but a conductive carbon compound is preferable. Use of the conductive carbon compound makes the electroconductivity of the electrode high and makes it easy for the reaction efficiency and the like to be raised.

The porous carbon more specifically includes mesoporous carbon, activated carbon, carbon black such as Ketjen black and acetylene black, carbon nanotube, graphite and graphene; and among these, carbon black is preferable and among the carbon black, conductive carbon black is more preferable.

(Nitrogen-Containing Aromatic Compound)

The active particle-containing catalyst of the present invention may further have a component derived from a nitrogen-containing aromatic compound. When the active particle-containing catalyst has a component derived from a nitrogen-containing aromatic compound, it is easy to improve the conversion efficiency, the selectivity and the like in synthesis of the carbonyl compound.

The component derived from the nitrogen-containing aromatic compound has a nitrogen element, and it is suitable that the nitrogen element is coordinated to the metal element constituting the active particle (for example, the metal element constituting a metal oxide) to form a metal-nitrogen element bond by a coordinate bond.

It is suitable that the component derived from the nitrogen-containing aromatic compound is supported on the porous carbon. That is, it is suitable that the component derived from the nitrogen-containing aromatic compound is coordinated to the metal element constituting the active particle, and is supported on the porous carbon.

It is preferable that the nitrogen-containing aromatic compound has a nitrogen-containing aromatic ring structure in which nitrogen is contained in the aromatic ring.

In the case where the active particle-containing catalyst contains the component derived from the nitrogen-containing aromatic compound, the active particle-containing catalyst can be obtained by heat-treating a mixture of the metal precursor, the porous carbon and the nitrogen-containing aromatic compound. Therefore, the component derived from the nitrogen-containing aromatic compound is a component obtained by heat-treating the nitrogen-containing aromatic compound.

In the present invention, due to that the heat treatment temperature is low as described later, the nitrogen-containing aromatic ring structure constituted of the nitrogen-containing aromatic compound remains also in the catalyst. Then, it is preferable that the component derived from the nitrogen-containing aromatic compound in the active particle-containing catalyst has the nitrogen-containing aromatic ring structure.

The nitrogen-containing aromatic compound includes pyridine derivatives, imidazole derivatives, pyrazole derivatives and triazole derivatives. Among these, preferable are pyridine derivatives, imidazole derivatives and pyrazole derivatives. These compounds may be used singly in one kind, or concurrently in two or more kinds.

Therefore, the catalyst may contain at least one selected from the group consisting of a pyridine ring structure, an imidazole ring structure, a pyrazole ring structure and a triazole ring structure, and among these, it is preferable that the catalyst contains at least one selected from the group consisting of a pyridine ring structure, an imidazole ring structure and a pyrazole ring structure.

The pyridine derivative to be used for the active particle-containing catalyst is a compound having a pyridine ring(s). The pyridine derivative may be a compound having one pyridine ring in one molecule (pyridine monomer), a compound having two pyridine rings, a compound having three pyridine rings, or a compound having four or more pyridine rings.

The pyridine monomer includes compounds which have at least one of functional groups such as an amino group ($-NH_2$), alkyl groups and alkoxy groups on a pyridine ring, and specifically includes alkylpyridines such as methylpyridine, ethylpyridine, butylpyridine and pentylpyridine (amylpyridine), alkoxypyridines such as methoxypyridine and butoxypyridine, and aminopyridines such as 4-aminopyridine. Among these, preferable are aminopyridines such as 4-aminopyridine, and ethylpyridine.

The compound having two pyridine rings in one molecule includes compounds (bipyridine derivatives) which have a bipyridine skeleton in which two pyridine rings are directly bonded through a carbon-carbon single bond, and includes bipyridines such as 2,2'-bipyridine. The compound having two pyridine rings in one molecule further includes bipyridine derivatives having an amino group, and specifically includes diaminobipyridine such as 4,4'-diamino-2,2'-bipyridine.

The compound having three pyridine rings in one molecule includes compounds (terpyridine derivatives) which have a terpyridine skeleton in which three pyridine rings are directly bonded through carbon-carbon single bonds. The terpyridine derivatives include terpyridine.

The compound having four or more pyridine rings in one molecule includes pyridine oligomers which have four or more pyridine rings and have a weight-average molecular weight of lower than 10,000. The pyridine oligomers include compounds which have a polypyridine skeleton in which pyridine rings are directly bonded through carbon-carbon single bonds. Suitable specific examples include polypyridine. The polypyridine includes poly(2,5-pyridine) and poly(3,5-pyridine), and among these, more preferable is poly(2,5-pyridine).

The molecular weight of the polypyridine such as poly(2,5-pyridine) is not especially limited, and is, in a weight-average molecular weight, preferably 500 or higher and 8,000 or lower, more preferably 1,000 or higher and 6,000 or lower and still more preferably 1,500 or higher and 5,000 or lower.

The pyridine derivatives also include polymers having a plurality of pyridine rings in one molecule and having a weight-average molecular weight of 10,000 or higher. It is suitable that the pyridine derivatives in this case have four or more pyridine rings in one molecule. As specific compounds, polyvinylpyridines, which are polymers of vinylpyridines, are also preferable and among the polyvinylpyridines, poly(4-vinylpyridine) is more preferable.

It is preferable, from the viewpoint of the conversion efficiency, the selectivity and the like, that the polyvinylpyridine such as the poly(4-vinylpyridine) has a molecular weight of not lower than a specified value; and the weight-average molecular weight is, for example, 1,000 or higher or 10,000 or higher, preferably 30,000 or higher and more preferably 50,000 or higher; and the weight-average molecular weight is, from the viewpoint of the easy availability and the like, for example, 200,000 or lower and preferably 100,000 or lower.

Here, the weight-average molecular weight is a value measured by gel permeation chromatography (GPC) in which polystyrene may be used as standard materials.

As the pyridine derivatives, among the above, more preferable are 4-aminopyridine, 2,2'-bipyridine, poly(2,5-pyridine), and poly(4-vinylpyridine) having a weight-average molecular weight of 10,000 or higher. Further, 4,4'-diamino-2,2'-bipyridine is also preferable.

The pyridine derivatives may be used singly in one kind or concurrently in two or more kinds.

The imidazole derivatives to be used for the active particle-containing catalyst are compounds having an imidazole ring(s). The imidazole derivatives may be compounds (imidazole monomers) having one imidazole ring in one molecule, compounds having two imidazole rings or compounds having three or more imidazole rings.

Examples of the imidazole monomers include compounds which has at least one functional group such as an amino group ($-NH_2$), an alkyl group, an alkoxy group, a halogen group, an aryl group or an aralkyl group on the imidazole, and it may have a heterocycle structure containing an imidazole ring.

The imidazole monomer specifically includes 1-methylimidazole, 1-ethylimidazole, 1-propylimidazole, 1-isopropylimidazole, 1-butylimidazole, 1-phenethylimidazole, 2-methylimidazole, 2-ethylimidazole, 2-propylimidazole, 2-isopropylimidazole, 2-butylimidazole, 2-phenylimidazole, 4-methylimidazole, 4-ethylimidazole, 4-propylimidazole, 4-isopropylimidazole, 4-butylimidazole, 4-phenylimidazole, benzimidazole, 1-methylbenzimidazole and bifonazole.

The compounds having two imidazole rings in one molecule include compounds (biimidazole derivatives) having an imidazole skeleton in which two imidazole rings are bonded directly through a carbon-carbon single bond. Examples of the imidazole derivatives include biimidazole.

As the compounds having a plurality of imidazole rings in one molecule, preferable are polyvinylimidazoles, which are polymers of vinylimidazoles; and among the polyvinylimidazoles, more preferable are poly(4-vinylimidazole) and poly(N-vinylimidazole) and still more preferable is poly(4-vinylimidazole).

It is preferable, from the viewpoint of the conversion efficiency, the selectivity and the like, that the polyvinylimidazole such as the poly(4-vinylimidazole) has a molecular weight of not lower than a specified value; and the weight-average molecular weight is, for example, 1,000 or higher and preferably 10,000 or higher; and the weight-average molecular weight is, from the viewpoint of the easy availability and the like, for example, 200,000 or lower and preferably 100,000 or lower.

The imidazole derivatives may be used singly in one kind or concurrently in two or more kinds.

The pyrazole derivatives to be used for the active particle-containing catalyst are compounds having a pyrazole ring(s). The pyrazole derivatives may be compounds (pyrazole monomers) having one pyrazole ring in one molecule, compounds having two pyrazole rings or compounds having three or more pyrazole rings.

Examples of the pyrazole monomers include compounds which have at least one functional group such as an amino group ($-NH_2$), an alkyl group, an alkoxy group, an aryl group or an aralkyl group on a pyrazole ring. The pyrazole monomers specifically include 1-methylpyrazole, 1-ethylpyrazole, 1-propylpyrazole, 1-isopropylpyrazole, 1-butylpyrazole, 1-phenethylpyrazole, 3-methylpyrazole, 3-ethylpyrazole, 3-propylpyrazole, 3-isopropylpyrazole, 3-butylpyrazole, 3-phenylpyrazole, 1,3-dimethylpyrazole, 1,3-diethylpyrazole, 1,3-dipropylpyrazole, 1,3-diisopropylpyrazole, 1,3-dibutylpyrazole and 1,3-diphenethylpyrazole.

The pyrazole derivatives may be used singly in one kind or concurrently in two or more kinds.

The triazole derivatives to be used for the active particle-containing catalyst are compounds having a triazole ring(s). The triazole derivatives may be compounds (triazole monomers) having one triazole ring in one molecule, compounds having two triazole rings or compounds having three or more triazole rings.

Examples of the triazole monomers include compounds which have at least one functional group such as an amino group ($-NH_2$), an alkyl group or an alkoxy group on a triazole ring.

The compound having two triazole rings in one molecule includes compounds (bitriazole derivatives) which have a bitriazole skeleton in which two triazole rings are directly bonded through a carbon-carbon single bond. Examples of the bitriazole derivatives include bitriazole.

As the compound having a plurality of triazole rings in one molecule, preferable are polyvinyltriazoles, which are polymers of vinyltriazoles; and among the polyvinyltriazoles, poly(1-vinyl-1,2,4-triazole) is more preferable.

It is preferable, from the viewpoint of the conversion efficiency, the selectivity and the like, that the polyvinyltriazole such as the poly(1-vinyl-1,2,4-triazole) has a molecular weight of not lower than a specified value; and the weight-average molecular weight is, for example, 1,000 or higher and preferably 10,000 or higher; and the weight-average molecular weight is, from the viewpoint of the easy availability and the like, for example, 200,000 or lower and preferably 100,000 or lower.

The triazole derivatives may be used singly in one kind or concurrently in two or more kinds.

(Method for Producing the Active Particle-Containing Catalyst)

Next, a method for producing the active particle-containing catalyst will be described. The above-mentioned active particle-containing catalyst can be obtained by mixing the metal precursor and the porous carbon, and heat-treating the resultant mixture (hereinafter, referred to as "catalyst raw material mixture") containing the metal precursor and the porous carbon. In the case where the active particle-containing catalyst contains the component derived from the nitrogen-containing aromatic compound, nitrogen-containing aromatic compound may be further mixed with the metal precursor and the porous carbon and the catalyst raw material mixture may contain the metal precursor, the porous carbon and the nitrogen-containing aromatic compound.

The metal precursor is a compound which turns to the above-mentioned active particle by heat treatment. Therefore, it is suitable that the metal precursor is a precursor having the above-mentioned metal element selected from the group consisting of group 8 to group 11 elements, and the preferable metal element is as described above. The metal element to be used for the metal precursor may be used singly in one kind or concurrently in two or more kinds.

In the case of concurrent use of two or more kinds, preferable is concurrent use of two or more kinds of precursors having the above-mentioned metal element selected from the group consisting of group 8 to group 11 elements, or concurrent use of a precursor having the metal element selected from the group consisting of group 8 to group 11 elements and a precursor having a metal element other than group 8 to group 11 elements (for example, a metal element of period 4 elements).

In the case of concurrent use of two or more kinds of the metal precursors, it is suitable that the active particle-containing catalyst is obtained by mixing and heat-treating the two or more kinds of the metal precursors and the porous carbon; therefore, it is suitable that the catalyst raw material mixture contains two or more kinds of the metal precursors.

It is preferable that the metal precursor contains a metal ion. Further, it is suitable that the metal precursor is used, for example, in a form of a metal salt. The metal salt includes metal nitrate salts, metal sulfate salts, metal chlorides, metal bromides, metal iodides and metal acetate salts, and among these, metal chlorides and metal nitrate salts are preferable and from the viewpoint of being capable of forming a suitable active particle, metal nitrate salts are more preferable.

Here, specific examples of the metal nitrate salts and metal chlorides to be used in the metal precursor are the same as the metal salts to be used as the catalyst, so description thereof will be omitted. The metal salt may also be a hydrate.

The porous carbon and the nitrogen-containing aromatic compound to be used as raw materials in the present production method are as described above.

The content of the metal originated from the metal precursor in the catalyst raw material mixture is, with respect to the total amount of the catalyst raw material mixture, preferably 0.1% by mass or higher and 70% by mass or lower and more preferably 2% by mass or higher and 50% by mass or lower. By making the content to be in the above range, the metal is contained in the catalyst without being aggregated and catalytic active points are formed in a suitable amount. Hence, it becomes easy for the selectivity and the like in synthesis of the carbonyl compound to be raised and the reaction efficiency and the like become raised.

The content of the porous carbon in the catalyst raw material mixture is not especially limited, but is, with respect to the total amount of the catalyst raw material mixture, for example, 10% by mass or higher and 95% by mass or lower, preferably 20% by mass or higher and 85% by mass or lower and more preferably 30% by mass or higher and 80% by mass or lower. By making the content of the porous carbon to be in the above range, while the catalytic activity is well retained, there can suitably be supported the active particle and the component derived from the nitrogen-containing aromatic compound.

In the case of using the nitrogen-containing aromatic compound, it is preferable that the amount of the nitrogen-containing aromatic compound to be blended in the catalyst raw material mixture is adjusted so the molar ratio (nitrogen-containing aromatic ring/metal element) of the nitrogen-containing aromatic ring of the nitrogen-containing aromatic compound to the metal element originated from the metal precursor as to become 0.1 or higher and 30 or lower. By making the molar ratio to be in the above range, occurrence of side reactions is suppressed and the nitrogen element can be coordinated in a suitable amount to the metal of the active particle. Hence, it becomes easy for the selectivity, the conversion efficiency and the like in synthesis of the carbonyl compound to be raised. The molar ratio is more preferably 1 or higher and 20 or lower. Here, the molar ratio represents a ratio of the number of the nitrogen-containing aromatic ring contained in the nitrogen-containing aromatic compound and the molar number of the metal element contained in the metal precursor.

The temperature in heat treatment of the catalyst raw material mixture is preferably 150° C. or higher and 800° C. or lower. By making the heat treatment temperature to be in the above range, while formation of unnecessary by-products is suppressed, the catalyst raw material mixture can suitably be sintered. Hence, the active particle becomes enabled to be formed from the metal precursor and suitably supported on the porous carbon. Further, migration of the active particle is prevented and the particle size of the active particle can be made small and it becomes easy for the surface area and the like of the catalyst to be made large. In the case where the catalyst raw material mixture contains the nitrogen-containing aromatic compound, the nitrogen contained in the nitrogen-containing aromatic compound becomes enabled to be coordinated to the metal of the active particle and the component derived from the nitrogen-containing aromatic compound becomes enabled to be suitably supported on the porous carbon. Further, by making the heat treatment temperature to be made low as described above, it becomes easy for the nitrogen-containing aromatic ring structure of the nitrogen-containing aromatic compound to be retained also in the produced catalyst.

From the above viewpoints, the heat treatment temperature is preferably 180° C. or higher and 550° C. or lower and more preferably 200° C. or higher and 380° C. or lower.

The time of the heat treatment is not especially limited, but is, for example, 0.25 hour or longer and 10 hours or shorter, preferably 0.5 hour or longer and 8 hours or shorter and more preferably 1 hour or longer and 5 hours or shorter.

The heat treatment may be carried out in an inert gas atmosphere such as argon or nitrogen gas, or may be carried out in a reductive atmosphere such as hydrogen.

It is preferable that the catalyst raw material mixture to be heat-treated is powdery or particulate. When the catalyst raw material mixture is made to be powdery or particulate, the catalyst obtained by the heat treatment can also be made to be powdery or particulate. It is more preferable that the catalyst raw material mixture to be heat-treated is composed of the metal precursor and the porous carbon, or the metal precursor, the porous carbon and the nitrogen-containing aromatic compound.

It is suitable that the catalyst raw material mixture is obtained, for example, by fabricating a dilute liquid of the catalyst raw material mixture in which the metal precursor, the nitrogen-containing aromatic compound and the porous carbon are diluted with a diluting solvent, and drying the dilute liquid.

In the dilute liquid of the catalyst raw material mixture, it is preferable that each component (the metal precursor and the porous carbon, or the metal precursor, the nitrogen-containing aromatic compound and the porous carbon) is dispersed or dissolved in the diluting solvent. By making each component to be dispersed or dissolved in the diluting solvent, there can be obtained the catalyst raw material mixture in which each component is homogeneously mixed.

As the diluting solvent to be used for diluting the catalyst raw material mixture, water or an organic solvent can be used. The organic solvent includes ester-based solvents, ketone-based solvents, ether-based solvents, alcohol-based solvents, glycol ethers, amide-based solvents, nitrile-based solvents, carbonate-based solvents, halogenated hydrocarbons, hydrocarbons, sulfone-based solvents, sulfoxide-based solvents and formamide, but is not especially limited. Further as the diluting solvent, there may be used a mixed solvent of water and an organic solvent. The concentration of the dilute liquid of the catalyst raw material mixture is not especially limited, but is, for example, 0.01 g/L or higher and 25 g/L or lower and preferably 0.1 g/L or higher and 5 g/L or lower.

In the catalyst-containing electrolyte solution, the catalyst may dissolve or may not dissolve in an alcohol-based compound described later or a mixed liquid of the alcohol-based compound and a solvent, and it is suitable that the catalyst which does not dissolve is dispersed in the alcohol-based compound or the mixed liquid.

The content of the catalyst in the catalyst-containing electrolyte solution is not especially limited, and it is suitable to regulate the content such that the synthesis of the carbonyl compound progresses suitably. The specific content of the catalyst is, per 1 L of the catalyst-containing electrolyte solution, for example, 0.001 to 50 g, preferably 0.01 to 10 g and more preferably 0.05 to 1 g.

Here, the content of the catalyst, in the case where the metal salt is a hydrate, refers to an amount of the hydrate subtracted by the mass of water molecules in the hydrate.

[Redox Species]

In the present invention, the catalyst-containing electrolyte solution contains, in addition to the catalyst, the redox species. In the present invention, by making the electrolyte solution to contain, in addition to the catalyst, the redox species, in the electrochemical cell, even if the electrode for synthesizing the carbonyl compound is made to contain no catalyst as described later, unexpectedly, the organic carbonate, the organic oxalate or both thereof from carbon monoxide can be synthesized in a high selectivity.

As the redox species, there can be used, for example, one having a molecule or ion size smaller than the alcohol-based compound and having an oxidation-reduction activity. The redox species specifically includes halogenated metal salts, organic redoxes and complex redoxes.

The halogenated metal salts include halogenated lithium salts such as lithium chloride, lithium bromide and lithium iodide, halogenated sodium salts such as sodium chloride, sodium bromide and sodium iodide, halogenated potassium salts such as potassium chloride, potassium bromide and potassium iodide, halogenated cesium salts such as cesium chloride, cesium bromide and cesium iodide, and halogenated ammonium salts such as ammonium chloride, ammonium bromide and ammonium iodide.

The organic redoxes include TEMPO-based radical compounds such as 2,2,6,6-tetramethylpiperidin-1-oxyl (TEMPO) and 4-methoxy-2,2,6,6-tetramethylpiperidin-1-oxyl (MeO-TEMPO), and azaadamantane-N-oxyl (AZADO).

The complex redoxes include palladium-based complexes such as palladium acetylacetonate $(Pd(OAc)_2)$ and tetrakis (triphenylphosphine) palladium $(PdPPh_3)_4$ complex), and cobalt-based complexes such as tris(2,2'-bipyridine) cobalt $(Co(bpy)_3$ complex) and tris[1,3-bis(4-pyridyl)propane] cobalt $(Co(bpp)_3$ complex).

Among the above, as the redox species, preferable are halogenated lithium salts, and TEMPO-based radical compounds; and more preferable are lithium chloride, lithium bromide, TEMPO and MeO-TEMPO. Among these, from the viewpoint of raising the selectivity of the carbonyl compound, particularly the organic carbonate, lithium bromide and MeO-TEMPO are still more preferable.

The redox species may be used singly in one kind or concurrently in two or more kinds.

In the catalyst-containing electrolyte solution, the redox species may dissolve or may disperse in an alcohol-based compound described later or in a mixed liquid of the alcohol-based compound and a solvent, but it is preferable that the redox species dissolves therein.

The concentration of the redox species in the catalyst-containing electrolyte solution is not especially limited, and may be regulated such that the synthesis of the carbonyl compound progresses suitably. The specific concentration of the redox species is, for example, 0.001 to 5.0M, preferably 0.01 to 1.0M and more preferably 0.05 to 0.5M.

[Reactant (Alcohol-Based Compound)]

It is preferable that the catalyst-containing electrolyte solution further contains a reactant. In the present invention, as the reactant, an alcohol-based compound is used. The alcohol-based compound is a reactant which reacts with carbon monoxide in the electrochemical cell (typically, anode compartment) to form the organic carbonate, the organic oxalate or both thereof. It is suitable that the alcohol-based compound being the reactant, as described later, is filled in the electrochemical cell (typically, anode compartment).

The alcohol-based compound, in the environment where an electrochemical reaction is carried out in the electrochemical cell, may be any one of a solid, a liquid and a gas, but being a liquid is preferable. The alcohol-based compound being a liquid can easily be filled in the electrochemical cell even without using a solvent described later.

The alcohol-based compound is a compound having at least one hydroxyl group, and more specifically, is a compound represented by the following general formula (1). Here, in the present specification, the "alcohol-based compound" is a concept including also aromatic hydroxy compounds, represented by phenol, in which a hydroxyl group is bonded directly to an aromatic ring such as a benzene ring.

$$ROH \tag{1}$$

wherein R denotes an organic group having 1 to 15 carbon atoms.

The organic group having 1 to 15 carbon atoms R denotes in the above general formula (1) includes hydrocarbon groups having 1 to 15 carbon atoms. The hydrocarbon groups include alkyl groups having 1 to 15 carbon atoms, alkenyl groups having 2 to 15 carbon atoms and aryl groups having 6 to 15 carbon atoms.

The alkyl groups having 1 to 15 carbon atoms include a methyl group, an ethyl group, various propyl groups, various butyl groups, various pentyl groups, various hexyl groups, various heptyl groups, various octyl groups, various nonyl groups, various decyl groups, various dodecyl groups and various pentadecyl groups.

The alkenyl groups having 2 to 15 carbon atoms include a vinyl group, various propynyl groups, various butynyl groups, various pentynyl groups, various hexenyl groups, various heptenyl groups, various octenyl groups, various nonenyl groups, various decenyl groups, various dodecenyl groups and various pentadecenyl groups.

Here, the "various" means various isomers including n-, sec-, tert- and iso-. Further the alkyl groups and the alkenyl groups may be any of straight-chain, branched-chain and cyclic ones.

The aryl groups having 6 to 15 carbon atoms include a phenyl group and a naphthyl group. Here, the above hydrocarbon groups may have a substituent and in such a case the number of carbon atoms including also the substituent is 1 to 15.

The organic group having 1 to 15 carbon atoms in the general formula (1) may contain a heteroatom such as a nitrogen atom, an oxygen atom, a sulfur atom, a phosphorus atom or a halogen atom.

Among these, an oxygen atom is preferable. In the case of having an oxygen atom, it is preferable that the oxygen atom is either oxygen atom of a hydroxyl group and an ether bond. Therefore, it is preferable that R is a hydrocarbon group having at least either one of a hydroxyl group and an ether bond. It is preferable that the hydroxyl group is one in number in R. That is, the alcohol-based compound may have two hydroxyl groups.

The alcohol-based compound having two hydroxyl groups is, more specifically, preferably a group represented by the following formula (1-1).

$$HO-R^{11}-OH \quad (1\text{-}1)$$

wherein $R^{11}$ is a divalent saturated hydrocarbon group having 2 to 15 carbon atoms, but the number of carbon atoms of $R^{11}$ is preferably 2 to 4 and more preferably 2 or 3.

The compound represented by the above general formula (1) is preferably one in which R is, among the above, an alkyl group having 1 to 8 carbon atoms, an alkenyl group having 2 to 8 carbon atoms or an aryl group having 6 to 8 carbon atoms; and also preferable is a compound represented by the general formula (1-1) and having the number of carbon atoms of $R^{11}$ of 2 to 4.

Among these, the compound in which R is an alkyl group or an aryl group is more preferable and the compound in which R is an alkyl group is especially preferable. The number of carbon atoms of the alkyl group is more preferably 1 to 3, still more preferably 1 or 2 and most preferably 1.

Specifically, from the viewpoint of the reactivity and the production efficiency, preferable are methanol, ethanol, phenol, 1-propanol, ethylene glycol, propylene glycol and the like; and among these, methanol is more preferable.

The alcohol-based compound may be used singly in one kind or concurrently in two or more kinds.

[Formation of the Carbonyl Compound]

The reaction to be carried out in the electrochemical cell (typically, anode compartment) involves a first reaction in which the organic carbonate is formed from carbon monoxide and the alcohol-based compound, a second reaction in which the organic oxalate is formed from carbon monoxide and the alcohol-based compound, or both the reactions.

The first reaction is a carbonylation reaction in which the organic carbonate is formed; and specifically, an organic carbonate ($(RO)_2CO$) is formed by a reaction represented by the following formula (i).

$$CO+2ROH \rightarrow (RO)_2CO+2H^++2e^- \quad (i)$$

wherein R is the same as described above, but is preferably an alkyl group having 1 to 8 carbon atoms, an alkenyl group having 2 to 8 carbon atoms or an aryl group having 6 to 8 carbon atoms, more preferably an alkyl group or an aryl group, and still more preferably an alkyl group. The number of carbon atoms of the alkyl group is more preferably 1 to 3, still more preferably 1 or 2 and most preferably 1.

In the case where ROH is represented by the general formula (1-1), an organic carbonate is formed by a reaction represented by the following formula (ii).

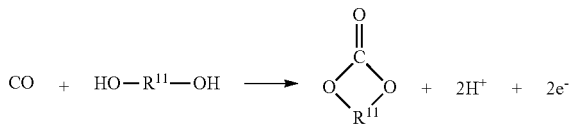
(ii)

wherein $R^{11}$ is the same as described above, but the number of carbon atoms of $R^{11}$ is preferably 2 to 4, more preferably 2 or 3 and still more preferably 2.

Specific preferable organic carbonates include one or two or more selected from the group consisting of dimethyl carbonate, diethyl carbonate, ethylene carbonate, dipropyl carbonate, propylene carbonate, diphenyl carbonate, ethyl methyl carbonate, methyl propyl carbonate and ethyl propyl carbonate; and among these, dimethyl carbonate is more preferable.

The second reaction is a reaction in which the organic oxalate represented by the following formula (2) is formed from carbon monoxide and the alcohol-based compound. Specifically, it is suitable that an organic oxalate represented by the formula (2) is synthesized by a reaction represented by the following formula (iii).

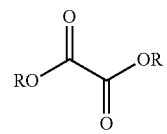
(2)

wherein R is the same as described above.

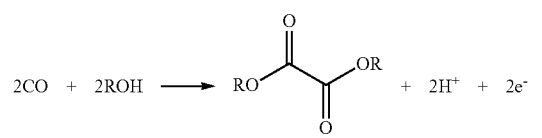
(iii)

wherein R is the same as described above.

In the case where ROH is represented by the general formula (1-1), an organic oxalate represented by the following formula (2-1) is formed by a reaction represented by the following formula (iv).

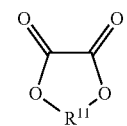
(2-1)

wherein $R^{11}$ is the same as described above.

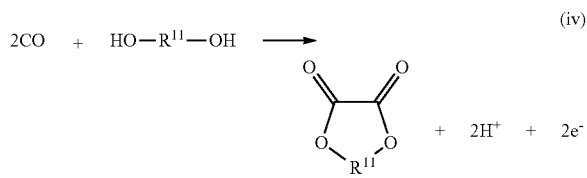
(iv)

wherein $R^{11}$ is the same as described above.

Specific preferable organic oxalates include one or two or more selected from the group consisting of dimethyl oxalate, diethyl oxalate, ethylene oxalate, dipropyl oxalate, propylene oxalate, diphenyl oxalate, ethyl methyl oxalate, methyl propyl oxalate and ethyl propyl oxalate. Among these, dimethyl oxalate is more preferable.

[Solvent]

In the case where the alcohol-based compound is a solid or a gas, in the case where the solubility of the redox species needs to be improved or in like cases, the catalyst-containing electrolyte solution may further contain a solvent. In this case, it is suitable that the alcohol-based compound is filled as a mixed liquid with the solvent (hereinafter, referred to simply also as "mixed liquid") in an anode compartment. Also, in the case where the alcohol-based compound is a liquid, the alcohol-based compound may be filled, of course, as a mixed liquid with the solvent.

As the solvent, a solvent usually used for the electrochemical reaction can be selected, and examples thereof include nitrile-based solvents such as acetonitrile, carbonate-based solvents such as ethylene carbonate, propylene carbonate, butylene carbonate, vinylene carbonate, dimethyl carbonate, ethyl methyl carbonate and diethyl carbonate, lactone-based solvents such as γ-butyrolactone, ether-based solvents such as 1,2-dimethoxyethane, 1-ethoxy-2-methoxyethane, 1,2-diethoxyethane, tetrahydrofuran and 2-methyltetrahydrofuran, phosphate ester solvents, phosphoric acids, sulfolane-based solvents and pyrrolidones. These solvents may be used singly in one kind or concurrently in two or more kinds.

[Electrode for Synthesizing the Carbonyl Compound (First Electrode)]

The electrode for synthesizing the carbonyl compound is an electrode to be used when the carbonyl compound is electrochemically synthesized from carbon monoxide. The electrode for synthesizing the carbonyl compound constitutes an anode in the electrochemical cell.

In the present invention, it is preferable that the electrode for synthesizing the carbonyl compound contains no catalyst. In order to make the electrode for synthesizing the carbonyl compound contain the catalyst, processes to make the catalyst to be supported on the electrode, involving applying a coating liquid containing the catalyst on an electrode base material, dipping the electrode base material in a dipping liquid containing the catalyst, or the like, are necessary; however, when the electrode for synthesizing the carbonyl compound contains no catalyst, these processes become unnecessary. Therefore, the carbonyl compound can be synthesized by a simple constitution.

Here, the catalyst is, as described above, a catalyst to catalyze the electrochemical reaction for synthesizing the organic carbonate, the organic oxalate or both thereof from carbon monoxide. Since the electrode for synthesizing the carbonyl compound contacts with the catalyst-containing electrolyte solution, the catalyst contained in the catalyst-containing electrolyte solution adheres to the electrode for synthesizing the carbonyl compound in some cases, but in the present specification, such an embodiment that the catalyst contained in the catalyst-containing electrolyte solution adheres to the electrode for synthesizing the carbonyl compound is not included in a feature "the electrode for synthesizing the carbonyl compound contains the catalyst".

The electrode for synthesizing the carbonyl compound is constituted, for example, of an electrode base material. The electrode base material is not especially limited, but includes carbon base materials, metal base materials and metal oxide base materials, and it is preferable that the electrode base material has electroconductivity. The base material may be a porous body. The base material is one to become a base material constituting the electrode, and suitably has, for example, a sheet shape or a plate shape.

Among the above, the carbon base material is preferable and porous carbon is more preferable. Specific examples of the porous carbon include carbon nonwoven fabrics. The carbon nonwoven fabrics are not especially limited, and already-known carbon nonwoven fabrics can be used. There can be used, for example, products thereof commercially available as carbon nonwoven fabrics for fuel cells, and the products include "Torayca"® Carbon Paper, manufactured by Toray Industries, Inc., "AvCarb 1071HCB", manufactured by New Metals and Chemicals Corporation, Ltd., and BC Series, manufactured by SGL Carbon AG.

The metal base materials include metal meshes, and metals to be used include gold, silver, platinum, nickel, titanium and chromium. The metal oxides to be used for the metal oxide base materials include indium oxide, tin oxide, tin-doped indium oxide and fluorine-doped tin oxide.

Further, the electrode for synthesizing the carbonyl compound may constitute a laminated assembly together with an ion exchange membrane and a second electrode (cathode) described later. It is suitable that the laminated assembly is a laminated assembly having the electrode (anode) for synthesizing the carbonyl compound, the ion exchange membrane and the second electrode (cathode) in this order. It is suitable that in the laminated assembly, the electrode (anode) for synthesizing the carbonyl compound and the second electrode (cathode) are joined through the ion exchange membrane to constitute a membrane-electrode assembly described later.

[Constitution of the Electrochemical Cell]

Next, referring to FIG. 1, one embodiment of the constitution of the electrochemical cell of the present invention will be described in more detail, but the constitution of the electrochemical cell is not limited to the following one embodiment.

(Anode Compartment)

As illustrated in FIG. 1, an electrochemical cell 10 according to one embodiment has an anode compartment 15. The anode compartment 15 is filled with the above-mentioned catalyst-containing electrolyte solution. In the anode compartment 15, an electrode (anode 11) for synthesizing the carbonyl compound is further disposed, and an electrolyte solution contacts with the anode 11.

Here, the inside of the anode compartment 15 may be wholly filled with the catalyst-containing electrolyte solution, or may have a partial space. The catalyst-containing electrolyte solution may be supplied through a first inlet port 15A described later to the anode compartment 15, or may be supplied through another inlet port (not shown in figure) to the anode compartment 15. The catalyst-containing electrolyte solution may be supplied in a state that each component constituting the catalyst-containing electrolyte solution has been mixed, to the anode compartment 15, or may be supplied as every component constituting the catalyst-containing electrolyte solution, to the anode compartment 15.

The anode compartment 15 is provided with the inlet port 15A, and carbon monoxide is supplied through the inlet port 15A. Here, the inlet port 15A through which carbon monoxide is supplied to the anode compartment 15 is referred to as first inlet port in some cases. Carbon monoxide is supplied as a gas.

A supply path such as a pipe is connected to the inlet port 15A, and the anode compartment 15 is connected to a carbon monoxide supply source or the like not shown in figure through the supply path, and carbon monoxide is supplied from the carbon monoxide supply source or the like. In the supply path, a flow rate control mechanism or the like may be disposed to control the flow rate of carbon monoxide supplied.

Carbon monoxide may be supplied continuously to the anode compartment 15, or may be supplied intermittently to the anode compartment 15. Carbon monoxide may be supplied alone to the anode compartment 15, or may be supplied as a gas carried on an inert carrier gas such as helium to the anode compartment 15. Further, carbon monoxide may be supplied together with carbon dioxide gas and the like.

The anode compartment 15 may be provided with an outlet port 15B for discharging formed substances, unreacted reactants, carbon monoxide and the like.

Carbon monoxide may be supplied by being subjected to bubbling or the like to the catalyst-containing electrolyte solution filled in the anode compartment 15. Further, carbon monoxide may react with the alcohol-based compound in the anode compartment 15 while at least a part of the carbon monoxide is dissolved in the catalyst-containing electrolyte solution filled in the anode compartment 15.

As described above, the catalyst and the redox species do not dissolve in the electrolyte solution in some cases, but in such a case, they may be dispersed in the electrolyte solution by a dispersing member installed in the electrochemical cell. Specifically, the catalyst, the redox species or both thereof may be dispersed in the electrolyte solution by bubbling of carbon monoxide, or may be dispersed by bubbling of a gas other than the carbon monoxide. Alternatively, the catalyst and the redox species may be dispersed in the electrolyte solution by installing a stirring device such as a stirring blade in the anode compartment 15 and mixing the electrolyte solution, or installing a circulation passage whose outlet side and inlet side are both connected to the anode compartment 15 and fluidizing the electrolyte solution by circulating the electrolyte solution through the circulation passage. Alternatively, the electrochemical cell may be made into a flow cell and the catalyst and the redox species may be dispersed in the electrolyte solution by fluidizing the electrolyte solution.

(Cathode Compartment)

It is suitable that the electrochemical cell 10 has, in addition to the anode compartment 15, a cathode compartment 16 in which a cathode 12 is disposed. The cathode compartment 16 is a region where an introduced reducible material is electrochemically reduced. The reducible material may be carbon dioxide or the like, or may be any other compound as long as it can be reduced in the cathode 12 side, and examples thereof include water, CO, $N_2$ and a proton. The cathode compartment 16 may be filled with the reducible material, or may be filled with the electrolyte solution. The electrolyte solution may be one containing the reducible material.

The cathode 12 is not especially limited, but may have a reduction catalyst to catalyze reduction, or may also be, for example, one in which a reduction catalyst is contained in the electrode base material. It is preferable that the reduction catalyst is a carbon dioxide reduction catalyst to catalyze the reduction reaction to reduce carbon dioxide to carbon monoxide. The cathode 12 may contain no reduction catalyst and may be composed of the electrode base material. The detail of the electrode base material is as described above.

It is suitable that the cathode compartment 16 is provided with a second inlet port 16A through which the reducible material and the like is supplied, and a second outlet port 16B or the like for discharging a reductant and the unreduced reducible material is discharged.

The electrochemical cell 10, as illustrated in the constitution of FIG. 3 described later, may further has a supply path 31 to connect the cathode compartment 16 and the anode compartment 15, and a reductant such as carbon monoxide obtained in the cathode compartment 16 may be supplied through the supply path 31 to the anode compartment 15.

(Ion Exchange Membrane)

It is suitable that the electrochemical cell 10 has further an ion exchange membrane 13. The ion exchange membrane 13 constitutes a diaphragm to separate the anode compartment 15 and the cathode compartment 16. In one embodiment illustrated in FIG. 1, the cathode 12 and the anode 11 are disposed at both sides of the ion exchange membrane 13, respectively, and are joined, and constitute a membrane-electrode assembly 14 together with the ion exchange membrane 13. As the ion exchange membrane 13, a solid membrane is used, which includes cation exchange membranes which cations such as protons can pass though, and anion exchange membranes which anions such as hydroxide ions can pass though.

The cation exchange membranes include ones which have, as a functional group, at least any one of a sulfonyl group, a carboxyl group, a phosphate group, and a silicate group. Cation exchange membranes having a sulfonyl group as a functional group include hydrocarbon resin-based polysulfonic acids such as polyethylene sulfonic acid and fullerene-crosslinked polysulfonic acid, and fluororesin-based sulfonic acids such as perfluoroethylene sulfonic acid. Perfluoroethylene sulfonic acid includes copolymers of tetrafluoroethylene and perfluoro[2-(fluorosulfonylethoxy) propyl vinyl ether]. Commercially available products thereof include "Nafion" (trademark of Dupont de Nemours, Inc.).

Cation exchange membranes having a carboxyl group as a functional group include polycarboxylic acids such as polyacrylic acid. As cation exchange membranes having a phosphate group or a silicate group as a functional group, there can also be used heteropolyacids such as silicotungstic acid and phosphotungstic acid. Further as the cation exchange membranes, there can be used phosphate glasses such as $SiO_2$—$P_2O_5$, and ceramics such as perovskite-type oxides.

The anion exchange membranes include resins and polyethers having a quaternary ammonium salt, such as poly(styrylmethyltrimethylammonium chloride), and polymers having an imidazolium group. Examples of the resins having an ammonium salt include "FAA-3-50", manufactured by FuMa-Tech GmbH, and "TM1 Durion Grade", manufactured by Orion Polymer Corp. The polymers having an imidazolium group include styrene-based polymers having an imidazolium group, and specifically include copolymers (PSMIM) of styrene and 1-(p-vinylbenzyl)-3-methyl-imidazolium, copolymers (PSTMIM) of styrene and 1-(p-vinylbenzyl)-tetramethyl-imidazolium, and copolymers (PSDMIM) of styrene and 1-(p-vinylbenzyl)-2,3-dimethyl-imidazolium.

In the present embodiment, for example, cations such as protons are generated at the anode 11 and the cations are sent to the cathode 12 side through the ion exchange membrane 13. Hence, it is preferable to use a cation exchange membrane as the ion exchange membrane 13.

An electric power source 19 is connected to the anode 11 and the cathode 12, and a voltage is applied between the anode 11 and the cathode 12. On application of the voltage, in the anode compartment 15, carbon monoxide introduced from the first inlet port 15A and the alcohol-based compound in the anode compartment 15 electrochemically react to thereby form the organic carbonate, the organic oxalate or both thereof. In the cathode compartment 16, a reducible material is reduced on the cathode 12 to form a reductant.

The electrochemical cell of the present invention is not limited to the constitution having been described in the above as long as having the electrode for synthesizing the carbonyl compound, and the electrolyte solution containing the redox species and the catalyst. In the above description, for example, although the cathode 12 and the anode 11 are joined on both sides of the ion exchange membrane 13, respectively, and constitutes the membrane-electrode assembly with the ion exchange membrane 13, there is no need of constituting a membrane-electrode assembly and the ion exchange membrane 13 and the electrode are not needed to be joined and are allowed to have another constitution.

FIG. 2 illustrates an electrochemical cell 20 having another constitution. In the electrochemical cell 20, an electrolyte solution 22 is filled in an electrochemical compartment 21, and an anode 11 and a cathode 12 are disposed in the electrolyte solution 22. However, the anode 11 and the cathode 12 do not need to be disposed in the electrolyte solution 22, as long as the contact with the electrolyte solution 22 is secured.

An ion exchange membrane 13 is disposed in the electrochemical compartment 21, and an electrolyte solution 22 is divided into a region (anode compartment) of the anode 11 side and a region (cathode compartment) of the cathode 12 side by the ion exchange membrane 13. In the electrochemical cell 20, the anode 11, the cathode 12 and the ion exchange membrane 13 are disposed separately from each other.

It is suitable that the electrolyte solution 22 contains the redox species, the catalyst and the alcohol-based compound, and the electrolyte solution 22 may further contain a solvent and the like as required. Here, the electrolyte solutions 22 may be the same in the anode compartment and the cathode compartment, but do not need to be the same, and an electrolyte solution in the anode compartment and an electrolyte solution in the cathode compartment may be different as long as the electrolyte solution 22 filled in the anode compartment contains the redox species, the catalyst and the alcohol-based compound.

The electrochemical cell 20 is provided with a first inlet port 15A, and an end of the first inlet port 15A is disposed in the electrolyte solution 22 in the region of the anode 11 side. A voltage is applied between the cathode 12 and the anode 11 by an electric power source 19.

Similarly, in the electrochemical cell 20 having such a constitution, carbon monoxide introduced from the inlet port 15A and the alcohol-based compound contained in the electrolyte solution are reacted in the region of the anode 11 side to thereby form the organic carbonate, the organic oxalate, or both thereof. On the cathode 12, it is suitable that there are reduced, a reducible material in the electrolyte solution 22 or a reducible material introduced from a second inlet port (not shown in figure) to the region of the cathode 12 side. In the case where the reducible material is gas, the reducible material may be blown into the electrolyte solution 22 of the cathode 12 side from the second inlet port not shown in figure.

The electrochemical cells 10, 20 described in the above are of course exemplary electrochemical cells, and the electrochemical cell of the present invention is not limited to the above constitutions. For example, in the electrochemical cell 20 having the constitution of FIG. 2, the ion exchange membrane may be omitted. Further, the constitution may be configured, for example, to apply a voltage by a photoelectromotive force.

Further, the electrochemical cell 10, 20 may be provided with a reference electrode or the like in the region (anode compartment or cathode compartment) of the anode 11 side or the cathode 12 side. It is suitable that the reference electrode is disposed so as to contact with the electrolyte solution contained in the anode compartment or the cathode compartment.

[Synthesis System]

The present invention also provides a synthesis system equipped with the above electrochemical cell. It is suitable that the synthesis system has a conversion portion which converts carbon dioxide into carbon monoxide and a supply path which supplies the carbon monoxide obtained in the conversion portion to the anode compartment. The present synthesis system, since being able to synthesize the carbonyl compound from carbon monoxide, can decrease the emission of carbon dioxide and prevent the global warming.

As the carbon dioxide, preferable is one obtained from any exhaust gas of electric power plants, ironworks, cement factories and waste incineration plants. Since in these facilities, an exhaust gas containing carbon dioxide in a large amount is generated, by using the exhaust gas generated in these facilities as a raw material, it becomes easy for the carbonyl compound such as the organic carbonate to be efficiently and practically produced.

FIG. 3 illustrates one embodiment of the present synthesis system. Referring to FIG. 3, there will be described in more detail a synthesis system according to the present invention and a method for producing the carbonyl compound from carbon dioxide.

As illustrated in FIG. 3, a synthesis system 30 is equipped with the electrochemical cell 10, and as described above, the organic carbonate, the organic oxalate or both thereof are formed from carbon monoxide and the alcohol-based compound in the anode compartment 15 in the electrochemical cell 10.

The cathode compartment 16 functions as a conversion portion which converts carbon dioxide into carbon monoxide; therefore, it is preferable that the cathode 12 contains a carbon dioxide reduction catalyst to reduce carbon dioxide to carbon monoxide.

Further, it is suitable that the synthesis system 30 is equipped with a supply path 31 (first supply path 31) to connect the cathode compartment 16 and the anode compartment 15, and it is suitable that the first supply path 31 supply carbon monoxide obtained in the cathode compartment 16 (conversion portion) to the anode compartment 15 through a first inlet port 15A.

Further, it is suitable that the synthesis system 30 has a carbon dioxide supply source 33. The carbon dioxide supply source 33 is not especially limited as long as being capable of supplying a gas containing carbon dioxide to the cathode compartment 16 (conversion portion), but it is preferable that the carbon dioxide supply source 33 is any one of electric power plants, ironworks, cement factories and waste incineration plants. In these facilities, an exhaust gas is generated in a large amount, but since the exhaust gas usually contains carbon dioxide, it is suitable that the exhaust gas generated in these each facility is supplied to the electrochemical cell 10. It is suitable that a gas containing carbon dioxide supplied from the carbon dioxide supply source 33 is supplied from a second inlet port 16A to the cathode compartment 16 through a second supply path 32.

It is suitable that the synthesis system 30 is equipped further with a carbon dioxide refining apparatus 34. The carbon dioxide refining apparatus 34 is an apparatus to refine a gas containing carbon dioxide of an exhaust gas or the like, supplied from the carbon dioxide supply source 33, to raise the carbon dioxide concentration of a gas to be supplied. That is, it is suitable that the gas containing carbon dioxide formed by the carbon dioxide supply source 33 is raised in the carbon dioxide concentration by the carbon dioxide refining apparatus 34, and then, is supplied to the cathode compartment 16 (conversion portion) through the second supply path 32. In the present embodiment, due to the installation with the carbon dioxide refining apparatus 34, carbon monoxide can be formed efficiently in the cathode compartment 16 (conversion portion) and the carbonyl compound can thereby be formed in a high efficiency in the anode compartment 15.

Specific examples of the carbon dioxide refining apparatus include apparatuses utilizing chemical adsorption methods using an amine compound, and physical adsorption methods.

The synthesis system 30 may be provided with a purification apparatus and the like not shown in figure other than the carbon dioxide refining apparatus 34. It is suitable that the purification apparatus removes impurities from the gas containing carbon dioxide supplied from the carbon dioxide supply source 33, and it is suitable that the gas from which impurities have been removed is supplied to the cathode compartment 16 (conversion portion). As the purification apparatus, various types of filters, and scrubbing columns are exemplified.

The synthesis system 30 may be equipped further with a product refining apparatus 35, an alcohol-based compound supply source 36 or the other(s). The product refining apparatus 35 is an apparatus to refine a product produced in the electrochemical cell 10 and discharged from an outlet port 15B. As the product refining apparatus 35, distillation columns and column devices are exemplified. Typically, since the carbonyl compound is discharged together with compounds (impurities) other than the carbonyl compound from the outlet port 15B, it is suitable that the impurities are removed or separated from the carbonyl compound to refine the carbonyl compound in the product refining apparatus 35. In the case where in the electrochemical cell 10 both the organic carbonate and the organic oxalate are synthesized, the organic oxalate and the organic carbonate may suitably be separated in the product refining apparatus 35.

The alcohol-based compound supply source 36 is a tank, a vessel or the like to hold the alcohol-based compound, and it is suitable that to the anode compartment 15, the alcohol-based compound is supplied from the alcohol-based compound supply source 36.

The synthesis system 30 having been described hitherto is only shown as one embodiment to produce the carbonyl compound by using the electrochemical cell of the present invention, and may have any constitution as long as not impairing the advantageous effects of the present invention; for example, the carbon dioxide refining apparatus 34, the product refining apparatus 35 and the like may suitably be omitted.

Further, the embodiment has been shown in which the cathode compartment 16 is used as the conversion unit to convert carbon dioxide into carbon monoxide, but any unit other than the cathode compartment 16 may be used as the conversion portion. For example, it is suitable that in an electrolytic cell other than the electrochemical cell 10, carbon dioxide is converted into carbon monoxide.

Further, in the synthesis system 30, an electrochemical cell does not need to be the electrochemical cell 10 having the membrane-electrode assembly, and it may also be the electrolytic cell 20 illustrated in FIG. 2.

EXAMPLES

The present invention will be described in more detail by way of Examples, but the present invention is not any more limited to these Examples.

Example 1

In an anode compartment of a two-compartment diaphragm-type electrolytic cell, there were disposed an electrode (anode) composed of a carbon paper (product name: "Sigracet 29 BC", manufactured by SGL Carbon AG) and a reference electrode composed of Ag/AgCl; in a cathode compartment, an electrode (cathode) composed of Pt was set; and the anode compartment and the cathode compartment were separated by Nafion, which was an ion exchange membrane. Thereafter, the anode compartment was filled with, as an electrolyte solution, 30 ml of a methanol solution in which 0.2M of LiBr as a redox species and 3 mg of $PdCl_2$ (Sigma-Aldrich Corp.) as a catalyst were dissolved in methanol. The cathode compartment was filled with 30 ml of a methanol solution of 0.2M of LiBr.

CO (1 atm) was supplied to the anode compartment, and a voltage of +1 V was applied between the electrodes to cause the reaction to occur; thereafter, components of the reaction liquid were analyzed by gas chromatography and by comparing the result of the analysis and the current value, the selectivity was calculated. The selectivity was calculated for the organic carbonate and the organic oxalate. The results are shown in Table 1.

Examples 2 to 8

In each Example, the selectivity was calculated as in Example 1, except for altering the redox species and the catalyst contained in the electrolyte solution in the anode compartment to those as described in Table 1. Here, as in Example 1, the concentration of the redox species in the electrolyte solution was made to be 0.2M; the amount of the catalyst, to be 3 mg.

TEMPO used was "TEMPO", manufactured by Sigma-Aldrich Corp.; MeO-TEMPO used was "4-Methoxy-TEMPO", manufactured by Sigma-Aldrich Corp.; and $HAuCl_4$ used was one manufactured by Sigma-Aldrich Corp.

Example 9

60 mg of $Pd(NO_3)_2 \cdot 2H_2O$ (manufactured by Sigma-Aldrich Corp.) and 60 mg of Ketjen black (product name: "EC-300J" (Fuel Cell Store), BET specific surface area: 800 $m^2/g$, average primary particle diameter: 40 nm) were dispersed in 50 ml of an ion-exchange water, thereafter dried, and heated at 300° C. for 1 hour to thereby obtain a catalyst (Pd/C) in which active particles of Pd were supported on a porous carbon.

A two-compartment diaphragm-type electrolytic cell was prepared as in Example 1, and the anode compartment was filled with 30 ml of an electrolyte solution in which 0.2M of LiBr as a redox species and 3 mg of the catalyst (Pd/C) were dispersed in methanol. The cathode compartment was filled with 30 ml of a methanol solution of 0.2M of LiBr, and the selectivity was calculated as in Example 1.

Examples 10 to 12

In each Example, the selectivity was calculated as in Example 9, except for altering the redox species and the catalyst contained in the electrolyte solution to those as described in Table 1. Here, as in Example 9, the concentration of the redox species in the electrolyte solution was made to be 0.2M; the amount of the catalyst, to be 3 mg.

The catalyst (Au/C) used in Examples 11, 12 was produced by dispersing 24 mg of $AuCl_3$ (manufactured by Sigma-Aldrich Corp.) and 60 mg of Ketjen black in 50 ml of an ion-exchange water, thereafter drying, and heating the resultant at 300° C. for 1 hour.

Example 13

35 mg of $Pd(NO_3)_2 \cdot 2H_2O$ (manufactured by Sigma-Aldrich Corp.), 51 mg of $HAuCl_4 \cdot 3H_2O$ (manufactured by Sigma-Aldrich Corp.), and 60 mg of Ketjen black were dispersed in 50 ml of an ion-exchange water, thereafter dried, and heated at 300° C. for 2 hours to thereby obtain a catalyst ($Pd_{50}Au_{50}$/C).

A two-compartment diaphragm-type electrolytic cell was prepared as in Example 9, and the anode compartment was filled with 30 ml of an electrolyte solution in which 0.2M of LiBr as a redox species and 3 mg of the catalyst ($Pd_{50}Au_{50}$/C) were dispersed in methanol. The cathode compartment was filled with 30 ml of a methanol solution of 0.2M of LiBr, and the selectivity was calculated as in Example 9.

Examples 14 to 20

In each Example, the selectivity was calculated as in Example 9, except for altering the redox species and the catalyst contained in the electrolyte solution to those as described in Table 1. Here, as in Example 9, the concentration of the redox species in the electrolyte solution was made to be 0.2M; the amount of the catalyst, to be 3 mg.

Then, each catalyst used in Examples 15 to 20 was produced as follows.

[$Pd_{50}Ag_{50}$/C]

The catalyst was obtained by dispersing 50 mg of $Pd(NO_3)_2 \cdot 2H_2O$ (manufactured by Sigma-Aldrich Corp.), 32 mg of $AgNO_3$ (manufactured by Sigma-Aldrich Corp.) and 60 mg of Ketjen black in 50 ml of an ion-exchange water, thereafter drying, and heating the resultant at 300° C. for 2 hours.

[$Ir_{80}Au_{20}$/C]

The catalyst was obtained by dispersing 50 mg of Ir(III) $Cl_3$ (manufactured by Sigma-Aldrich Corp.), 16 mg of $HAuCl_4 \cdot 3H_2O$ (manufactured by Sigma-Aldrich Corp.) and 60 mg of Ketjen black in 50 ml of an ion-exchange water, thereafter drying, and heating the resultant at 300° C. for 2 hours.

[$Ir_{50}Au_{50}$/C]

The catalyst was obtained by dispersing 31 mg of Ir(III) $Cl_3$ (manufactured by Sigma-Aldrich Corp.), 40 mg of $HAuCl_4 \cdot 3H_2O$ (manufactured by Sigma-Aldrich Corp.) and 60 mg of Ketjen black in 50 ml of an ion-exchange water, thereafter drying, and heating the resultant at 300° C. for 2 hours.

[$Ir_{80}Rh_{20}$/C]

The catalyst was obtained by dispersing 55 mg of Ir(III) $Cl_3$ (manufactured by Sigma-Aldrich Corp.), 14 mg of $Rh(NO_3)_3 \cdot xH_2O$ (manufactured by Sigma-Aldrich Corp.) and 60 mg of Ketjen black in 50 ml of an ion-exchange water, thereafter drying, and heating the resultant at 300° C. for 2 hours.

[$Ir_{50}Rh_{50}$/C]

The catalyst was obtained by dispersing 40 mg of Ir(III) $Cl_3$ (manufactured by Sigma-Aldrich Corp.), 40 mg of $Rh(NO_3)_3 \cdot xH_2O$ (manufactured by Sigma-Aldrich Corp.) and 60 mg of Ketjen black in 50 ml of an ion-exchange water, thereafter drying, and heating the resultant at 300° C. for 2 hours.

Comparative Examples 1 to 4

In each Comparative Example, the evaluation was carried out as in Example 1, except for not containing one of the redox species and the catalyst as described in Table 1, and altering the kinds of the redox species and the catalyst to those as described in Table 1.

TABLE 1

| | Electrolyte Solution Redox Species | Electrolyte Solution Catalyst | Organic Carbonate | Selectivity (%) | Organic Oxalate | Selectivity (%) |
|---|---|---|---|---|---|---|
| Example 1 | LiBr | $PdCl_2$ | dimethyl carbonate | 55 | dimethyl oxalate | 2 |
| Example 2 | LiCl | $PdCl_2$ | dimethyl carbonate | 53 | dimethyl oxalate | 4 |
| Example 3 | TEMPO | $PdCl_2$ | dimethyl carbonate | 24 | dimethyl oxalate | 41 |
| Example 4 | MeO-TEMPO | $PdCl_2$ | dimethyl carbonate | 36 | dimethyl oxalate | 42 |
| Example 5 | LiBr | $HAuCl_4$ | dimethyl carbonate | 38 | dimethyl oxalate | 11 |
| Example 6 | LiCl | $HAuCl_4$ | dimethyl carbonate | 33 | dimethyl oxalate | 10 |
| Example 7 | TEMPO | $HAuCl_4$ | dimethyl carbonate | 12 | dimethyl oxalate | 46 |
| Example 8 | MeO-TEMPO | $HAuCl_4$ | dimethyl carbonate | 34 | dimethyl oxalate | 48 |
| Example 9 | LiBr | Pd/C | dimethyl carbonate | 64 | dimethyl oxalate | 5 |
| Example 10 | MeO-TEMPO | Pd/C | dimethyl carbonate | 43 | dimethyl oxalate | 30 |
| Example 11 | LiBr | Au/C | dimethyl carbonate | 39 | dimethyl oxalate | 8 |

TABLE 1-continued

| | Electrolyte Solution Redox Species | Electrolyte Solution Catalyst | Organic Carbonate | Selectivity (%) | Organic Oxalate | Selectivity (%) |
|---|---|---|---|---|---|---|
| Example 12 | MeO-TEMPO | Au/C | dimethyl carbonate | 36 | dimethyl oxalate | 40 |
| Example 13 | LiBr | $Pd_{50}Au_{50}/C$ | dimethyl carbonate | 68 | dimethyl oxalate | 7 |
| Example 14 | MeO-TEMPO | $Pd_{50}Au_{50}/C$ | dimethyl carbonate | 55 | dimethyl oxalate | 6 |
| Example 15 | LiBr | $Pd_{50}Ag_{50}/C$ | dimethyl carbonate | 69 | dimethyl oxalate | 10 |
| Example 16 | MeO-TEMPO | $Pd_{50}Ag_{50}/C$ | dimethyl carbonate | 57 | dimethyl oxalate | 24 |
| Example 17 | LiBr | $Ir_{80}Au_{20}/C$ | dimethyl carbonate | 55 | dimethyl oxalate | 13 |
| Example 18 | MeO-TEMPO | $Ir_{50}Au_{50}/C$ | dimethyl carbonate | 52 | dimethyl oxalate | 38 |
| Example 19 | LiBr | $Ir_{80}Rh_{20}/C$ | dimethyl carbonate | 45 | dimethyl oxalate | 10 |
| Example 20 | MeO-TEMPO | $Ir_{50}Rh_{50}/C$ | dimethyl carbonate | 43 | dimethyl oxalate | 35 |
| Comparative Example 1 | LiBr | — | dimethyl carbonate | 0 | dimethyl oxalate | 0 |
| Comparative Example 2 | MeO-TEMPO | — | dimethyl carbonate | 0 | dimethyl oxalate | 0 |
| Comparative Example 3 | — | $PdCl_2$ | dimethyl carbonate | 2 | dimethyl oxalate | 0 |
| Comparative Example 4 | — | $HAuCl_4$ | dimethyl carbonate | 3 | dimethyl oxalate | 0 |

Note:
in the catalyst column of Examples 13 to 20 in Table 1, a numerical value indicated on the right side of a metal represents a content (% by mol) of the metal.

As indicated in Table 1, in each Example, by using an electrolyte solution containing a redox species and a catalyst in the electrochemical cell, the organic carbonate, the organic oxalate or both thereof could be synthesized electrochemically in a high selectivity from carbon monoxide and the alcohol-based compound. By contrast, in each Comparative Example, since an electrolyte solution containing both a redox species and a catalyst was not used, the organic carbonate, the organic oxalate or both thereof could not be synthesized electrochemically in a high selectivity.

EXPLANATION OF LETTERS AND NUMERALS 10, 20 ELECTROCHEMICAL CELL
11 ANODE (ELECTRODE FOR SYNTHESIZING CARBONYL COMPOUND)
12 CATHODE
13 ION EXCHANGE MEMBRANE
14 MEMBRANE-ELECTRODE ASSEMBLY
15 ANODE COMPARTMENT
16 CATHODE COMPARTMENT
15A, 16A INLET PORT
15B, 16B OUTLET PORT
19 ELECTRIC POWER SOURCE
21 ELECTROCHEMICAL COMPARTMENT
22 ELECTROLYTE SOLUTION
30 SYNTHESIS SYSTEM
31 SUPPLY PATH (FIRST SUPPLY PATH)
32 SUPPLY PATH (SECOND SUPPLY PATH)
33 CARBON DIOXIDE SUPPLY SOURCE
34 CARBON DIOXIDE REFINING APPARATUS
35 PRODUCT REFINING APPARATUS
36 ALCOHOL-BASED COMPOUND SUPPLY SOURCE

The invention claimed is:

1. An electrochemical cell which electrochemically synthesizes at least one carbonyl compound selected from the group consisting of organic carbonates and organic oxalates from carbon monoxide,
   the electrochemical cell comprising: an electrolyte solution comprising a redox species and a catalyst; and an electrode,
   wherein the catalyst comprises an active particle having a metal element and a support which supports the active particle thereon.

2. The electrochemical cell according to claim 1, wherein the metal element of the catalyst comprises at least one metal element selected from the group consisting of group 8 to group 11 elements.

3. The electrochemical cell according to claim 1, wherein the metal element of the catalyst comprises at least two metal elements selected from the group consisting of group 8 to group 11 elements.

4. The electrochemical cell according to claim 1, wherein the redox species is at least one selected from the group consisting of halogenated metal salts, organic redoxes and complex redoxes.

5. The electrochemical cell according to claim 1, wherein the electrode comprises no catalyst.

6. The electrochemical cell according to claim 1, wherein the electrolyte solution comprises an alcohol-based compound.

7. The electrochemical cell according to claim 1, further comprising: an anode compartment comprising the electrode disposed therein and containing the electrolyte solution therein; and an inlet port through which carbon monoxide is supplied to the anode compartment.

8. The electrochemical cell according to claim 1, comprising a dispersing member bubbling, fluidizing or stirring the electrolyte solution to disperse at least either one of the catalyst and the redox species in the electrolyte solution.

9. A synthesis system comprising an electrochemical cell according to claim 1,
wherein the synthesis system comprises a conversion portion which converts carbon dioxide to carbon monoxide and a supply path which supplies the carbon monoxide obtained by the conversion portion to the anode compartment.

10. The synthesis system according to claim 9, wherein the carbon dioxide is obtained from any one of exhaust gases of electric power plants, ironworks, cement factories and waste incineration plants.

11. The electrochemical cell according to claim 1, wherein the catalyst contained in the electrolyte solution catalyzes an electrochemical reaction for synthesizing the at least one carbonyl compound from the carbon monoxide.

12. The electrochemical cell according to claim 1, wherein the support is porous carbon which is a powdery or particulate carbon.

13. A method of producing a carbonyl compound, comprising electrochemically synthesizing at least one carbonyl compound selected from the group consisting of organic carbonates and organic oxalates from carbon monoxide in an electrochemical cell according to claim 1.

14. The method of producing a carbonyl compound according to claim 13, comprising converting carbon dioxide into carbon monoxide, the carbonyl compound being electrochemically synthesized from the carbon monoxide.

15. The method of producing a carbonyl compound according to claim 14, wherein the carbon dioxide is obtained from any one of exhaust gases of electric power plants, ironworks, cement factories and waste incineration plants.

* * * * *